United States Patent [19]

Cribbs

[11] 4,272,991
[45] Jun. 16, 1981

[54] SCANNING METHOD AND APPARATUS

[75] Inventor: Robert W. Cribbs, Placerville, Calif.

[73] Assignee: Litton Industrial Products, Inc., Beverly Hills, Calif.

[21] Appl. No.: 10,894

[22] Filed: Feb. 9, 1979

[51] Int. Cl.³ .................... A61B 10/00; G01N 29/04
[52] U.S. Cl. ........................................ 73/621; 128/660
[58] Field of Search .................... 73/619, 621, 640; 128/660

[56] References Cited

U.S. PATENT DOCUMENTS

| | | |
|---|---|---|
| 3,023,611 | 3/1962 | Howry .................................. 73/621 |
| 3,247,709 | 4/1966 | Gordon ................................. 73/621 |
| 3,480,002 | 11/1969 | Flaherty et al. .................. 73/621 X |
| 3,990,300 | 11/1976 | Kossoff ............................. 73/621 X |
| 4,078,435 | 3/1978 | Kossoff et al. ...................... 73/621 |

Primary Examiner—Charles A. Ruehl
Attorney, Agent, or Firm—Robert A. Seldon

[57] ABSTRACT

A scanner for use in ultrasonic imaging systems of the type which translates a transducer assembly along a path of successive positions. The scanner rotates the assembly during translation and, in one embodiment, rotates the transducer about a center of rotation which is offset from the center of translation.

8 Claims, 4 Drawing Figures

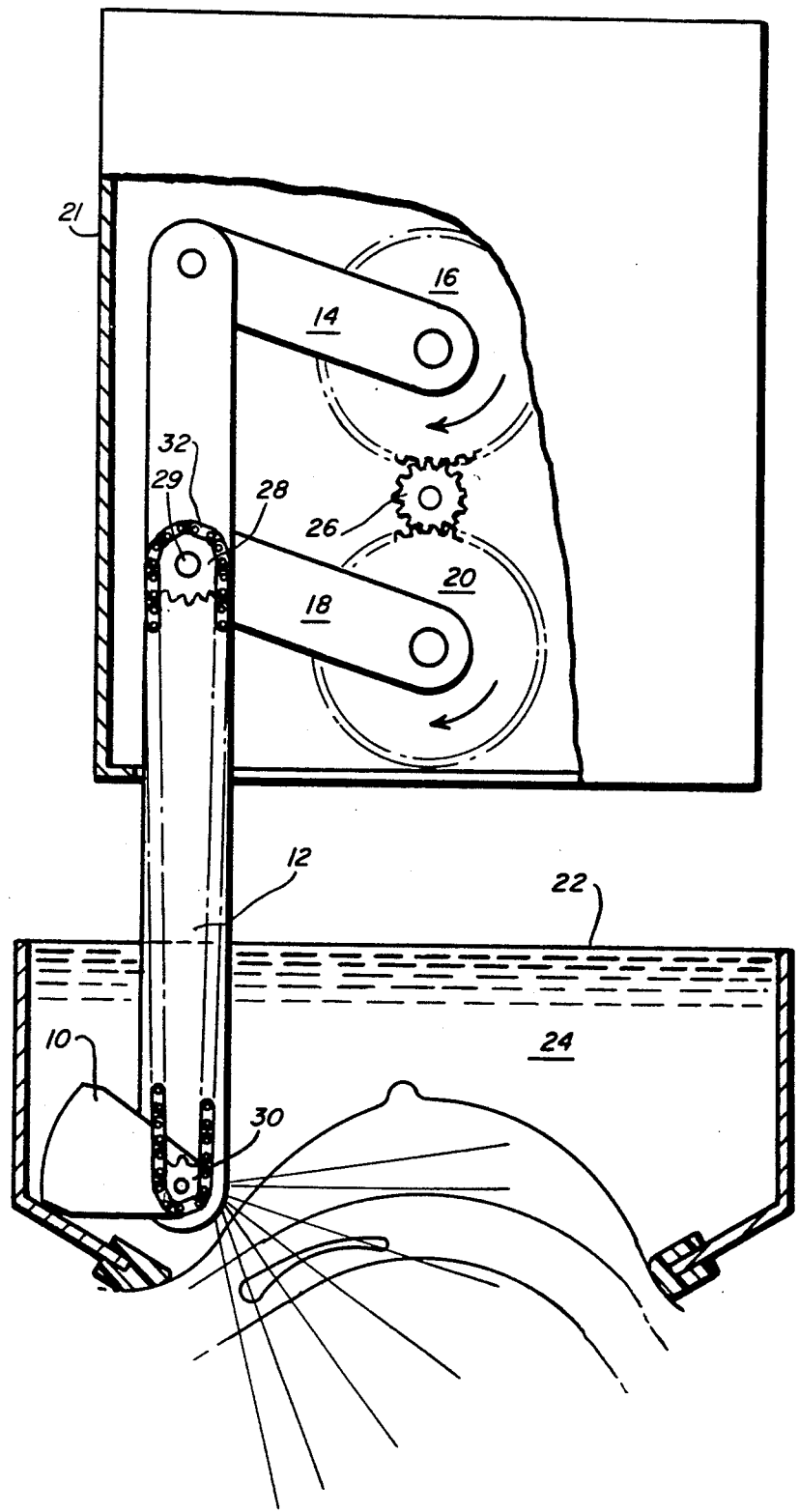
Fig_1

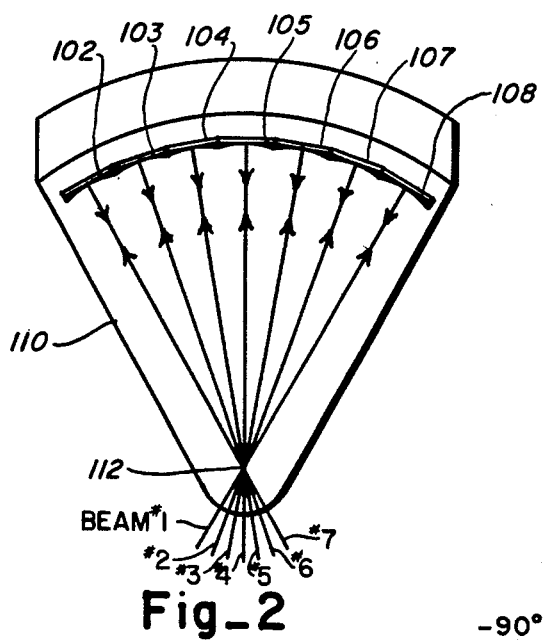
Fig_2
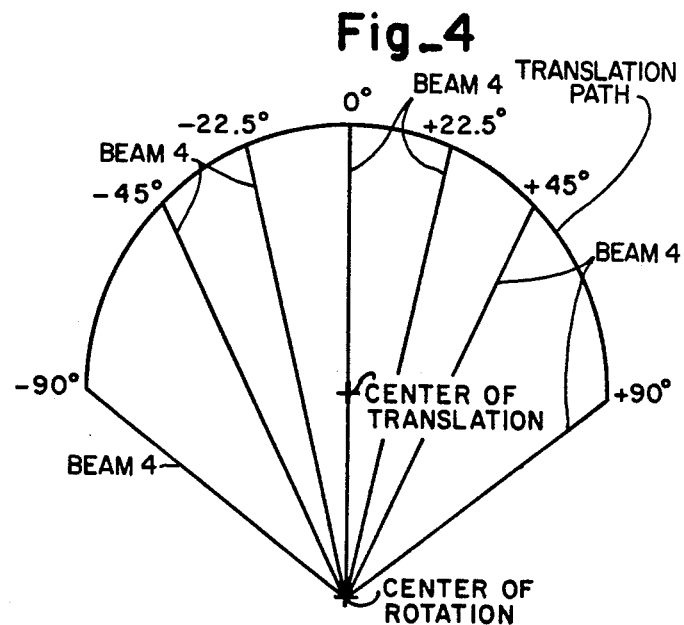
Fig_4
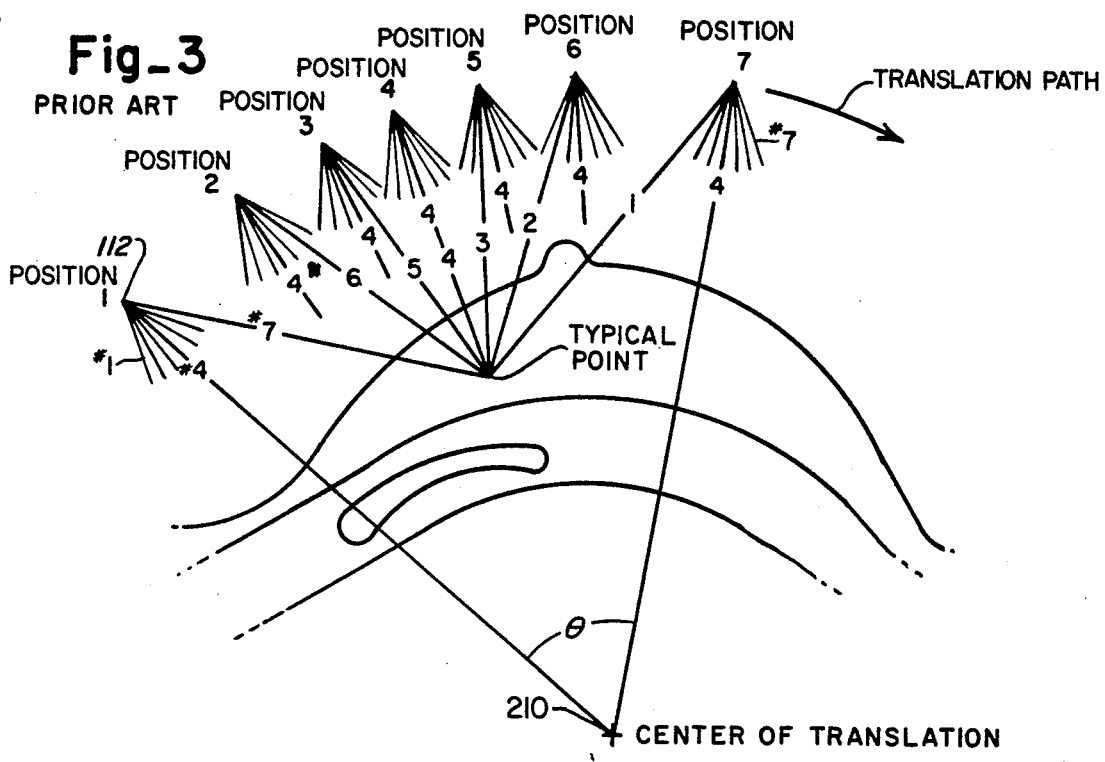
Fig_3 PRIOR ART

SCANNING METHOD AND APPARATUS

FIELD OF THE INVENTION

This invention relates to imaging systems of the pulse reflection type, such as ultrasound imaging systems, wherein pulses launched into an examined region are partially reflected by discontinuities in the propagation path. The reflection amplitudes are indicative of the respective magnitudes of density changes represented by the discontinuities, while the return times of the reflections indicate the respective distances from the transducer to the discontinuities.

This invention more particularly relates to the scanning portion of the imaging system which includes transducer means for generating the pulses and receiving the reflections and means for storing the data derived from the reflections.

As known in the art, two types of ultrasound scans are used: simple and compound. A simple scan occurs when the pulse beam is translated generally perpendicular to itself in a single pass across the tissue in such a way that every point in the examined tissue is in the center of the beam only once. A compound scan occurs when the angular direction of the beam oscillates as the transducer is translated. With compound scanning, each point in the tissue is in the beam several times.

Cancerous lesions generally have higher attenuation than noncancerous lesions. The attenuation is manifested by the "acoustic shadow" cast by the lesion. Only the simple scan is useful in determining the attenuation of ultrasound within a lesion; the characteristic shadow does not occur with compound scans because tissue behind the lesion will be registered by beams that strike it without going through the lesion.

However, simple scans will yield incomplete images because of the dependence of echo amplitudes, in the case of specular reflectors, on their orientation, with the result that only tissue interfaces nearly normal to the direction of the beam will be imaged. A compound scan is needed to register all specular reflectors in the breast.

Compound scanners, particularly for high speed imaging, typically employ phased linear arrays or phased curved arrays. Although phased arrays, theoretically, have high resolution and linear arrays can be focused to achieve good resolution, both of these lack two important qualities needed for good images: a large dynamic range, comparable to B-scans, and the ability to record, on a single picture, information derived by "looking" at tissues from multiple angles. The dynamic range limitation is significant because, when a reflected signal is registered, it creates weak artifacts at other points in the image plane. Real reflections producing echoes weaker than the artifacts cannot be registered, being obscured by the artifacts. Small lesions produce weak reflections, so a large dynamic range of reflections must be recorded if small lesions are to be detected.

SUMMARY OF THE INVENTION

A transducer that produces both simple and compound scans simultaneously is accordingly provided. A single probe generates a plurality of beams, preferably seven, rather than the usual single beam. As the probe is moved, from the region of the sternum to the axilla, for example, the transducer elements are activated in a sequence such as 1, 2, 3, 4, 5, 6, 7, 4, wherein one of the plurality is repeated to end the sequence.

Each sequence is used to create two images, The "compound" image is created by the plurality; then the repeated beam is used to form the simple scan image.

The echoes obtained are recorded on a scan converter to produce grey scale images in any manner known in the art. The compound scan may conveniently be recorded on one half of the scan converter target, the simple scan on the other. With this technique, the two images are guaranteed to be of the same tissue plane, and corresponding areas in the two images can be compared with certainty that they represent the same area in the tissue.

As the scanner is moved to the next plane, the image may be stored on video tape or in a system memory, and the scan converter erased in proportion for the next scan.

Another feature of the invention relates to the manner in which the transducer array is rotated during translation. One technique is to translate the array along a generally circular arc while rotating the array to maintain the central beam in alignment with the center of the circle of translation. In other words, the angular rate of rotation would equal the angular rate of translation. The result, however, as described in more detail below, is that the sector to be examined is not covered by all of the transducer's elements during the entire scan. I have discovered that this problem is solved by rotating the transducer at a less-than-equal rate, compared to the angular translation rate, which is preferably one-half the rate.

Further details concerning the invention may be found in the following description of a preferred embodiment of which the following figures form a part.

BRIEF DESCRIPTION OF THE DRAWING

FIG. 1 is a diagram of a scanner mechanism employed by the present invention,

FIG. 2 illustrates a typical transducer array for use in the scanner of FIG. 1 in accordance with the invention, FIG. 3 illustrates the orientation of the transducer elements during translation of the array, and FIG. 4 illustrates the orientation of the transducer elements during translation of the array in accordance with a second aspect of the invention.

DETAILED DESCRIPTION OF THE PREFERRED EMBODIMENT

FIG. 1 is a diagram of a scanner mechanism employed by the present invention. A transducer array 10 is supported at one end of a support member such as scanning arm 12. The other end of the arm 12 is rotatably mounted on a transmission member such as a first coupling bar 14 which is, in turn, coupled to a first gear 16 for rotation therewith. The arm 12 is similarly coupled via a second coupling bar 18 to a second gear 20. The array 10 is thereby rigidly supported within the frame 21 during its translation hereinafter described.

An exemplary transducer array is illustrated in FIG. 2 for clarity and comprises seven transducer elements 102–108 mounted on a plate 110 to form an arc-like segment. The respective beams from adjacent elements converge at a 10° angle, meeting at an apex 112, located approximately 3½ inches from the elements. The beams diverge thereafter for propagation through the examined body.

The transducer array 10 is shown in FIG. 1 scanning a breast within a fluid container 22. The fluid 24, which acts as a coupling medium between the transducer and breast, is typically water which, owing to the natural buoyancy of the breast, permits the breast to assume its natural shape, thereby yielding meaningful mammograms. Although several techniques are known for scanning the breast in water, FIG. 1 illustrates the use of a container which is the subject matter of my patent application U.S. Ser. No. 009,663 entitled "Fluid Container for Use With Ultrasonic Imaging System", filed concurrently herewith and hereby incorporated by reference.

As will be apparent to those skilled in the art, the gears 16, 20 are simultaneously rotated clockwise via actuating gear 26 causing the arm 12 to move from the illustrated position along a generally circular translation path. At the same time, the transducer 10 is rotated by means of a gear and chain arrangement which comprises a third gear 28 rotatable in response to the rotation of bar 18, a fourth gear 30 mounted for rotation on the transducer end of the arm 12, and a chain 32, coupling the gears which couples the gear 30 for responsive rotation to the gear 28. The gear 28 is fixedly mounted on a hub 29 which is an integral part of the coupling bar 18 and which extends through a hole in the arm 12. Accordingly, the hub 29 and the gear 28 rotates within the hole of arm 12 as the gear 20 rotates, thereby acting through the chain 32 to rotate the gear 30. The transducer array 10 is mounted on the gear 30 for rotation therewith. The relationship between the rate of transducer rotation and the rate of translation is dependent on the gear ratios of the gear 28 and gear 30.

FIG. 3 illustrates the conventional orientations of representative transducer elements as they are rotated during the translation of a seven-element array along a scan path in a breast examination. The path of the translated apex 112 is shown to be along a circular arc having a center of translation 210 and to comprise a plurality of scan positions 1–7. The array is illustratively shown as the apex 112 and the beams 1–7 diverging therefrom as illustrated in FIG. 2. The array is depicted as being conventionally rotated at an angular rate equal to the angular rate of translation. Accordingly, the translation of the array from position 1 to position 7 through an angle $\theta$ would conventionally be accompanied by the rotation of the array 10 (FIG. 1) through a similar angle $\theta$ on the scanning arm 12 (FIG. 1). Consequently, the central beam (i.e. beam 4) would always pass through the center of translation 210.

From FIG. 3, it may be seen that the side beams will miss the examined regions when the transducer array is translated from its intermediate position. Thus, in location #1, beams 1–3 will miss the region while beams 5–7 will miss at position 7. The result is that a target within the breast will only be scanned a limited number of times from a limited number of angles, adversly affecting the resolution of the image.

FIG. 4 illustrates the orientation of the central transducer element 105, during translation of the array, in accordance with the invention. A generally circular translation path extending around a center of translation, and similar to the translation path previously illustrated in FIG. 3, is depicted. For purposes of clarity, however, the scan positions have been identified by their angular position from the reference position of 0°. The reference position has been arbitrarily chosen to be that which is vertically positioned above the center of translation. As illustrated in FIG. 4, the translation path extends from $-90°$, through the reference position, to $+90°$. For the sake of clarity, only the path of beam 4 has been illustrated for each of the scan path positions. As indicated in FIG. 4, the array is positioned on the arm 12 (FIG. 1) so that the central beam 4 passes through the center of translation at the 0° position. The array is rotated at a slower angular rate than the angular rate of translation, preferably one-half with respect to the reference path of beam 4 (i.e., the beamed path at the 0° position), the path of beam 4 is shown to be 45° when the array is at the $-90°$ or the $+90°$ translation path positions. The beam path is similarly at a $22\frac{1}{2}°$ angle, with respect to the reference path, at the $-45°$ and the $+45°$ positions. The respective paths of the central beam 4 are shown to intersect at a center of rotation which is displaced from the center of translation. The center of rotation is at a greater radial distance from the translation path than is the center of translation; specifically, twice the radial length when the angular rotation of the transducer array is at the preferred one-half rate of translation. In other words, the central transducer element accordingly rotates through an arc having twice the radius of the radius associated with the scan path. Consequently, the beams are confined to a narrower region within the breast and an image having greater resolution is obtained.

A previously indicated, the transducer may be utilized to simultaneously provide data representing a simple and a compound scan. The electronics necessary for such provision are with the knowledge of those skilled in the art and details are accordingly omitted for brevity.

While it is believed that the foregoing description is sufficient in detail to enable one skilled in the art to make and use the invention without the necessity of undue experimentation, it will be understood that the invention is not limited to those details presented. Naturally, other elements may be substituted and modifications or improvements made which become apparent to those skilled in the art upon reading this specification. It is therefore respectfully requested that the invention be broadly construed within the full spirit and scope of the appended claims.

I claim:

1. A scanner for use in an ultrasonic imaging system and of the type for translating a transducer assembly along a path of successive positions, each position being angularly referenced to a center of translation, wherein the scanner comprises:

means for rotating the transducer assembly about a center of rotation which is offset from the center of translation.

2. A scanner for use in an ultrasonic imaging system and of the type for translating a transducer assembly along a path of successive positions, each position being angularly referenced to a center of translation, wherein the scanner comprises: means responsive to the angular rate of translation for rotating the transducer assembly at a lesser rate of rotation.

3. The scanner of claim 2 wherein the angular rate of rotation is one-half the angular rate of translation.

4. The scanner of claim 1 or 2 including a frame member a support member a transmission member mounted for rotation within the frame member and coupled to the support member so as to impart a generally arc-like translation to the support member when rotated a transducer element mounted for translation with the support member and for rotation thereon means responsive to the rotation of the transmission member for rotating the transducer element at a less than equal rate of rotation.

5. The scanner of claim 4 wherein the rotation means includes
 a first gear mounted for rotation on the support member in response to the rotation of the transmission member,
 a second gear affixed to the transducer element for rotation therewith, and
 a chain for coupling the first and second gears.

6. In an ultrasonic imaging process wherein a transducer assembly is translated along a path of successive positions angularly referenced to a center of translation and the transducer assembly is rotated during translation, the improved step comprising rotating the transducer assembly about a center of rotation which is at a greater radial length from the transducer assembly than the center of translation.

7. The method of claim 6 wherein the transducer assembly is rotated at a rate which is less than the angular rate of translation.

8. The method of claim 7 wherein the rate of rotation is approximately one-half the rate of translation.

* * * * *